United States Patent [19]

Kessler

[11] Patent Number: 5,055,287
[45] Date of Patent: Oct. 8, 1991

[54] METHODS TO CONTROL COLOR DURING DISINFECTING PEROXIDASE REACTIONS

[76] Inventor: Jack H. Kessler, 23 Carriage House Path, Ashland, Mass. 01721

[21] Appl. No.: 151,909

[22] Filed: Feb. 3, 1988

Related U.S. Application Data

[63] Continuation-in-part of Ser. No. 946,907, Dec. 29, 1986, abandoned.

[51] Int. Cl.$^5$ .............. A61K 37/48; A61K 7/20; A01N 59/12; A01N 59/00
[52] U.S. Cl. .............. 424/7.1; 424/94.4; 424/53; 424/613; 424/616; 424/669; 424/405
[58] Field of Search .............. 424/7.1, 94.4, 53, 150, 424/130, 613, 616, 669; 435/28

[56] References Cited

U.S. PATENT DOCUMENTS

| | | | |
|---|---|---|---|
| 2,451,022 | 10/1948 | Dohrmann | 424/7.1 |
| 3,654,180 | 4/1972 | Bauer | 435/28 |
| 4,223,003 | 9/1980 | Scheller | 424/53 |
| 4,301,145 | 11/1981 | Cestari | 424/80 |
| 4,476,108 | 10/1984 | Kessler et al. | 424/94.4 |
| 4,576,817 | 3/1986 | Montgomery et al. | 424/94.4 |

OTHER PUBLICATIONS

Thomas et al., Antimicrob. Agts. Chemo. (Jun. 1978) vol. 13, No. 6 pp. 1000–1005.
Tietz, ed., Fundamentals of Clinical Chemistry, (1970), p. 159.
JACS, (1951), vol. 73, pp. 1842–1843.

*Primary Examiner*—Jacqueline M. Stone
*Attorney, Agent, or Firm*—E. Lieberstein

[57] ABSTRACT

This invention relates to a color controlled disinfecting peroxide cold sterilization composition employing an iodide salt and to a method for controlling the formation and duration of color when such composition is combined with water.

11 Claims, 10 Drawing Sheets

METHODS TO CONTROL COLOR DURING DISINFECTING PEROXIDASE REACTIONS

This is a continuation-in-part of U.S. patent application Ser. No. 946,907 filed Dec. 29, 1986, now abandoned.

INTRODUCTION

A peroxide cold sterilization system which uses the enzyme peroxidase to catalyze the transfer of electrons from donor molecules to peroxide molecules in an aqueous solution is taught in U.S. Pat. Nos. 4,476,231; 4,473,550; and 4,588,586. The preferred donor molecule is a salt of iodide preferably sodium or potassium iodide. A byproduct of the peroxidase catalyzed reduction of hydrogen peroxide using an iodide salt as a source of donor molecules may be the formation of colored species.

A variety of disinfecting applications prohibit the formation of colored species. Said colored species present objectionable organoleptic properties when the disinfection occurs on humans or animals. These colored species may unacceptably alter the product to be disinfected in solution such as a contact lens or denture. Also there may be a threshold level of color which is objectionable in any application where said colored species can be visually identified during said enzymatically catalyzed disinfecting reaction.

The term disinfection as used in the present invention means killing or rendering non-viable microscopic organisms found in nature. These organisms include, but are not limited to, Gram negative bacteria, Gram positive bacteria, fungi, and spores.

DESCRIPTION OF THE INVENTION

The peroxide sterilization systems is dependant upon the relative concentration of peroxidase, peroxide and iodide in solution. For any given application, it is often necessary to utilize relatively high concentrations of iodide. This invariably increases the problem of the formation of colored species during the course of the enzyme catalyzed reaction. It has been discovered that it is possible to control the formation of color when iodide is used as the donor molecule. The amount of color formed once the disinfecting peroxidase based chemistry of this application is initiated increases as the iodide concentration increases. The rate and effectiveness of the disinfecting peroxidase based chemistry of this application is usually positively correlated with the iodide concentration. Therefore, it is desirable to be able to reduce or eliminate the color contributed by the reaction between peroxidase, peroxide and iodide.

Color is defined as an increase in the spectral absorbance above a minimal threshold for a given application. In general this increase can be defined as an increase in abosrbance greater than 0.005 O.D. in a standard 1 cm cuvette as measured in a UV-VIS spectrophotometer falling in the wavelength range between 340 and 750 nanometers. That is, if the reaction generated by peroxidase, peroxide and iodide increases the absorbance of the reaction environment anywhere between 340 and 750 nanometers more than 0.005 O.D. then color is present. The absorbance maximum and shape of the absorbance spectrum generated by this system can vary depending upon the relative ratios and concentrations of the three components, and other variables such as ionic strength and temperature.

It has also been discovered that it is possible to control the duration of color formation so as to have the disinfecting solution become colored upon dissolution of, for instance, a pill in a liquid carrier and then have said solution turn colorless after the disinfecting cycle. Using an intrinsic color indicator to signal completion of a disinfection cycle confers a dramatic benefit to an end user of this technology in many applications.

The present invention contemplates the use of several mechanisms to control the formation and duration of color. One mechanism involves the addition of an agent to function as a decolorizer for the reaction between peroxidase, peroxide and iodide. Examples of suitable decolorizers include sorbic acid, malonic acid, boronic acid, and sodium chloride. The decolorizers can be added to the basic components of the peroxide system to form a color controlled disinfecting peroxide sterilization composition or can be introduced into the solution anytime during the reaction. The peroxide component may also be used as a decolorizer when present in a concentration above that required to fulfill the disinfecting application. For example to disinfect a contact lens the preferred peroxide concentration should be in a range of 0.0003 to 0.00003%. Additional peroxide can be added at a proferred range between 0.001% and 0.3% as a decolorizer to the extent that it will not cause eye irritation to the lens wearer.

A second mechanism which may be used alone or in combination with the first mechanism to control the formation of color includes limiting the concentration of the iodide salt to a level equal to or below the level corresponding to the designated minimum acceptable minimum color threshold level for the particular application and adding other donor molecules to supplement the disinfecting formulation requirements for the application.

A third mechanism to control color includes interupting the reaction between the components peroxidase, peroxide and the iodide salt upon reaching an acceptable color threshold for the particular application. The reaction may be interrupted in a variety of ways including neutralizing the reaction by the addition of agents which reduce hydrogen peroxide such as pyruvic acid, platinum, copper ions and catalase. Alternatively an agent may be added to compete with the iodide salt in the reaction. The competing agent's activity in solution may be timed to increase as the acceptable minimum color threshold level is approached.

The above mechanisms may be combined to supplement each other. For example, a decolorizer may be added to raise the minimum threshold level for unacceptable color formation in combination with the use of another donor molecule and/or a neutralizing agent.

The material used as a bactericide or disinfection agent in accordance with the method of this invention is a combination of a salt of iodide, a peroxide and a peroxidase which can be stored in any fashion which precludes the initiation of the enzymatic reaction. That is, the components of this invention can be stored by combination of any two components without the presence of the third; this precludes the possibility of enzymatic action and subsequent depletion of substrates. Alternately, all the components of this invention can be stored as a powder or pill. The stored components of this invention are subsequently combined and thereby activated by admixture in a suitable carrier. When, decolorizers are added they can also be predissolved in the carrier along with other components of the invention or they can be admixed as a component of a pill or powder.

Any solid entity which liberates hydrogen or methyl peroxide upon dissolution can serve as the source of peroxide. Alternately, one can dissolve the iodide salt and declolorizer(s) in a suitable carrier and make a pill containing peroxidase and a suitable source or peroxide.

DETAILED DESCRIPTION OF THE INVENTION

The peroxidase of this invention is identified by the International Union of Biochemistry and the International Union of Pure and Applied Chemistry by the Enzyme Commission identification No. E.C. 1.11.1.7.

Peroxidase can be obtained from a wide variety of sources. The least expensive and most robust peroxidase suitable for this application is horseradish peroxidase although lactoperoxidase can also be used. Commercially obtained peroxidase comes lyophilized as a dry powder. Alternatively, peroxidase can be dissolved in a suitable carrier for future admixture with its substrates.

The donor molecule of this invention is iodide. Suitable sources of iodide for this invention include sodium iodide and potassium iodide as well as other salts of iodide. Any compound which yields iodide ions upon dissolution in water, without yielding other deleterious effects to the activity of the system, is suitable for this application. The simple salts of iodide have the advantage of being inexpensive and they are very stable.

The oxidant of this invention is a compound which yields a peroxide upon dissolution in water or an appropriate carrier although peroxide can be directly formulated into a liquid product. The preferred oxidant of this invention is hydrogen peroxide. Alternatively, methyl peroxide can be formulated in the product. Suitable materials which can serve as precursors for hydrogen peroxide include metal peroxides, percarbonates, persulphates, perphosphates, peroxyesters, urea peroxide, peroxyacids, alkylperoxides, acylperoxides and perborates. Mixtures of two or more of these substances can also be used.

The decolorizers of this invention include a broad range of compounds. It has been found that certain soluble salts like sodium chloride or potassium chloride, or mixtures thereof, substantially reduces the color increase from the reaction between peroxidase, peroxide and iodide when the decolorizers are present in the 0.1 to 200 millimolar concentration range. It is to be understood that other alkali metal salts and alkali metal chlorides can often be substituted in whole or in part for the sodium or potassium chloride. Likewise, certain simple organic acids like sorbic acid have been found to reduce or eliminate the color formed by the reaction of peroxides with iodide and peroxide.

The decolorizers of this invention produce their action while maintaining both peroxidase activity and the disinfecting effect of the chemistry. Sodium pyruvate has been used to inactivate the peroxide based disinfection of contact lenses but this type of inactivation is distinct from the control of an unwanted by-product, color, which this application describes. Color produced by the reaction of peroxidase, peroxide and iodide can be controlled by stopping the reaction after a defined period of time by agents which inactivate peroxidase, consume peroxide or compete with iodide for the active site of peroxidase. However, this type of inactivation is different from that described in this application since its effect is to terminate the disinfecting reaction. Sodium pyruvate, platinum or copper are typical examples of agents which consume peroxide. Hydrazine and methyl hydroperoxide are examples of agents which inactivate peroxidase. Fluoride is an example of an agent which will compete with iodide for the active site of peroxidase. Other donor molecules will also compete with iodide for the active site of peroxidase but many of these molecules also yield color or are not suitable for a particular application. It is, however, possible to reduce the amount of color formed by substituting donor molecules like tyrosine.

Temporal control of color formation during the enzymatically catalyzed reduction of peroxide by peroxidase in the presence of iodide can be effected by formulating the relative concentrations of iodide and hydrogen peroxide. The greater the iodide concentration, all other things being equal, the more intense the color and the longer lasting the color. The concentration of hydrogen peroxide will effect the amount of color formed and shorten the time duration of color formation.

This invention deals with controlling color. The color intensity of a disinfecting reaction in the oral cavity must be controlled within an acceptable organoleptic range. In addition, the color present must not be so great as to stain or discolor the teeth. At component concentrations of 0.003% peroxide, 0.05 mg/ml peroxidase, 10 millimolar sodium phosphate (pH 7.0), a concentration of 0.1 mg/ml sodium iodide could be used in the oral cavity FIG. 2f) to maintain color at a suitable level.

EXAMPLES

EXAMPLE 1

Figure 1:
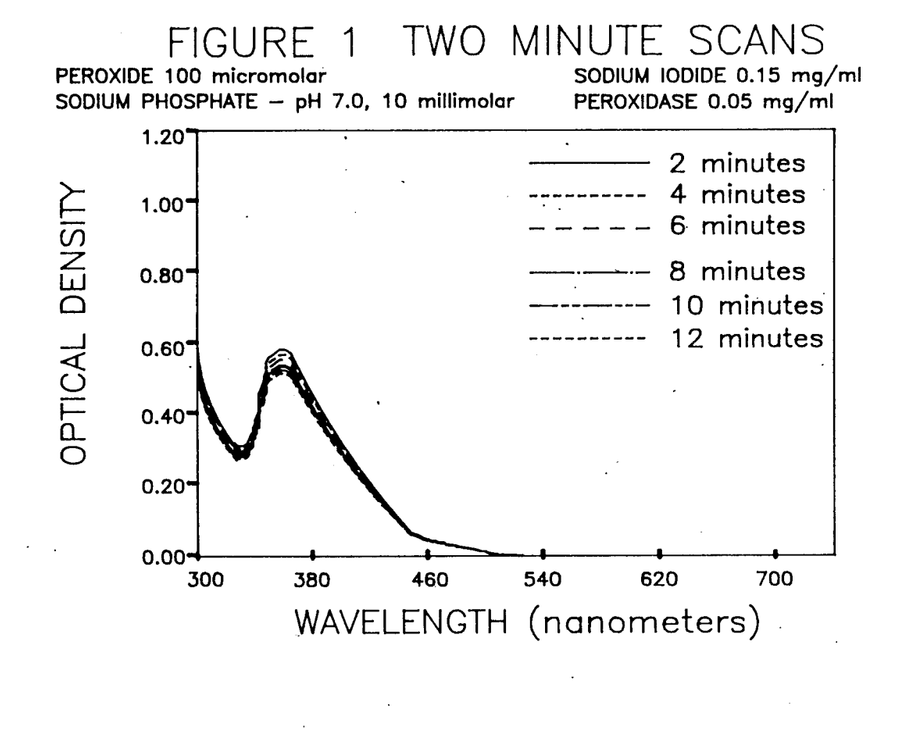

FIG. 1 shows UV-VIS spectrophotometric scans taken at two minute intervals on a Beckman 122 UV-VIS spectrophotometer. The volume was 3 ml containing the concentrations of components listed below.

| Concentration of Reagents For FIG. 1 | |
| --- | --- |
| Component | Concentration |
| peroxidase | 0.05 mg/ml |
| peroxide | 100 micromolar |
| sodium iodide | 0.15 mg/ml |
| sodium phosphate-pH 7.0 | 10 millimolar |

Figure 1A:
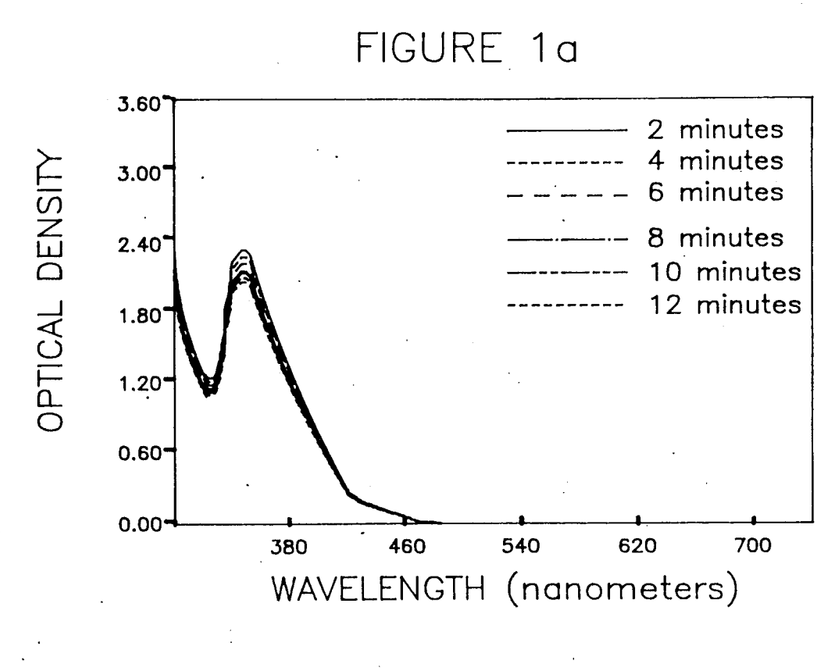

FIG. 1 shows a single absorbance peak of 0.550 optical density centered at 355 nm which does not change meaningfully in intensity over a 12 minute period. FIG. 1a shows identical scans taken at the following concentrations.

| Concentration of Reagents For FIG. 1a | |
| --- | --- |
| Component | Concentration |
| peroxidase | 0.05 mg/ml |
| peroxide | 100 micromolar |
| sodium iodide | 1.5 mg/ml |
| sodium phosphate-pH 7.0 | 10 millimolar |

Figure 1B:
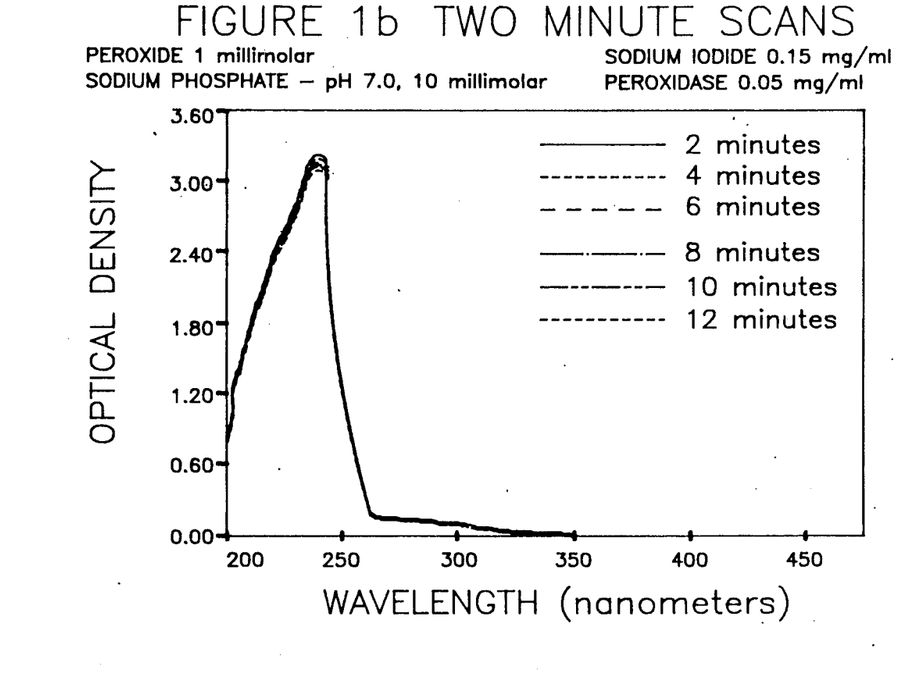

It is clear that the ten fold increase in sodium iodide concentration has increased the optical density to 2.25 O.D., an almost five fold increase. FIG. 1b shows the effect of increasing the effective concentration of peroxide ten fold to 1 millimolar at a concentration of sodium iodide of 0.15 mg/ml.

Concentration of Reagents For FIG. 1b

| Component | Concentration |
|---|---|
| peroxidase | 0.05 mg/ml |
| peroxide | 1 millimolar |
| sodium iodide | 0.15 mg/ml |
| sodium phosphate-pH 7.0 | 10 millimolar |

Figure 1C:
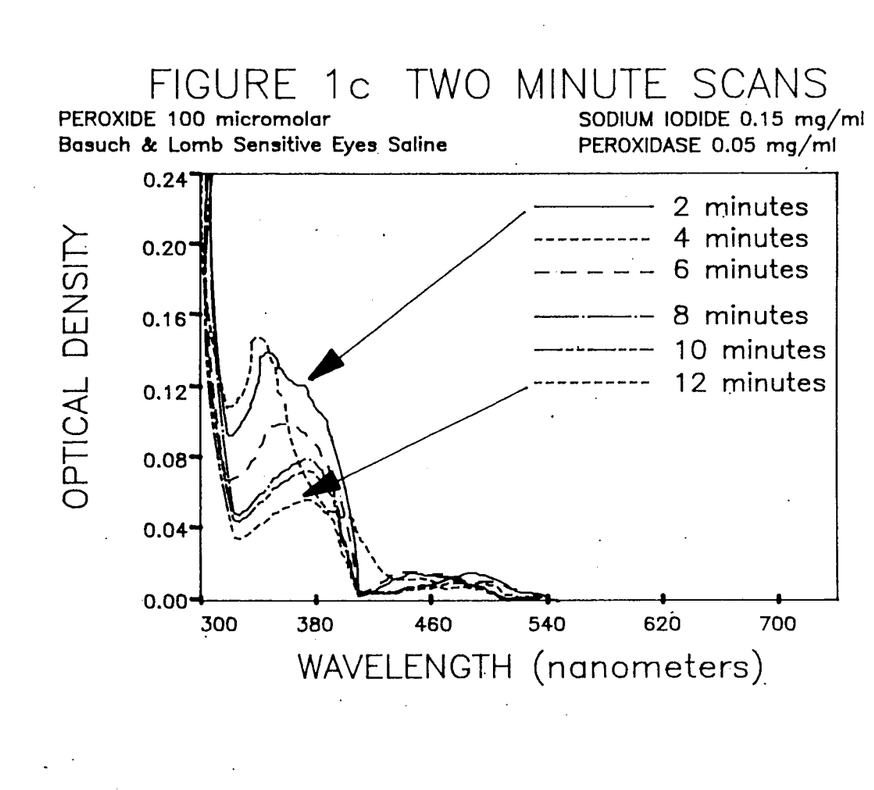

FIG. 1c shows the effect that a buffered medium can have on color formation. The reaction was run in Bausch & Lomb Sensitive Eyes Saline, Lot# GB506 with component concentrations listed below:

Concentration of Reagents For FIG. 1c

| Component | Concentration |
|---|---|
| peroxidase | 0.05 mg/ml |
| peroxide | 100 micromolar |
| sodium iodide | 0.15 mg/ml |

As compared to FIG. 1 the intensity of color is meaningfully decreased: maximum optical density 0.145 as compared to 0.55. Additionally, the color decreases significantly over a 12 minute time period to 0.073 optical density. That is, a level of temporal color control is effected.

EXAMPLE 2

Figure 2:
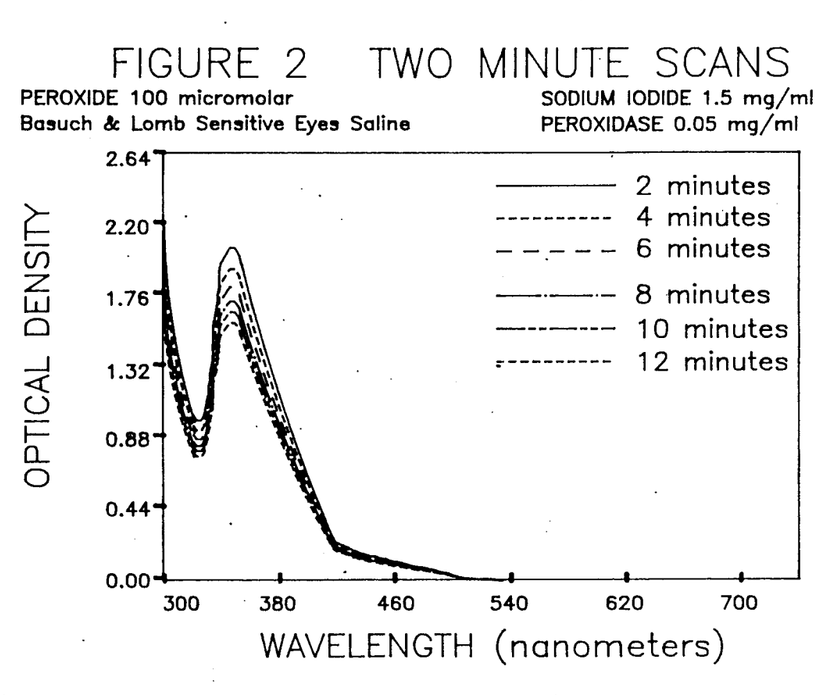
Figure 2A:
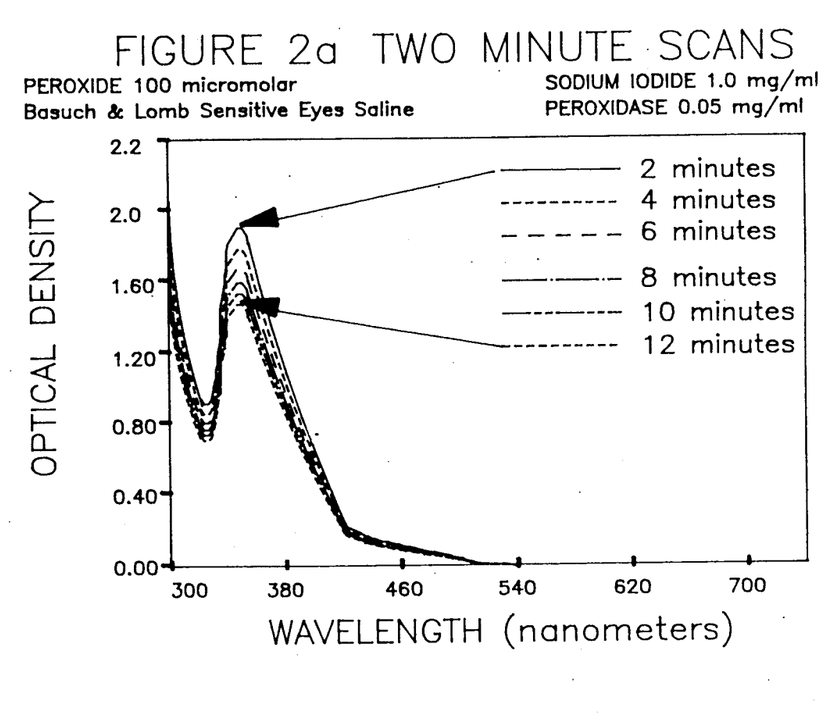
Figure 2B:
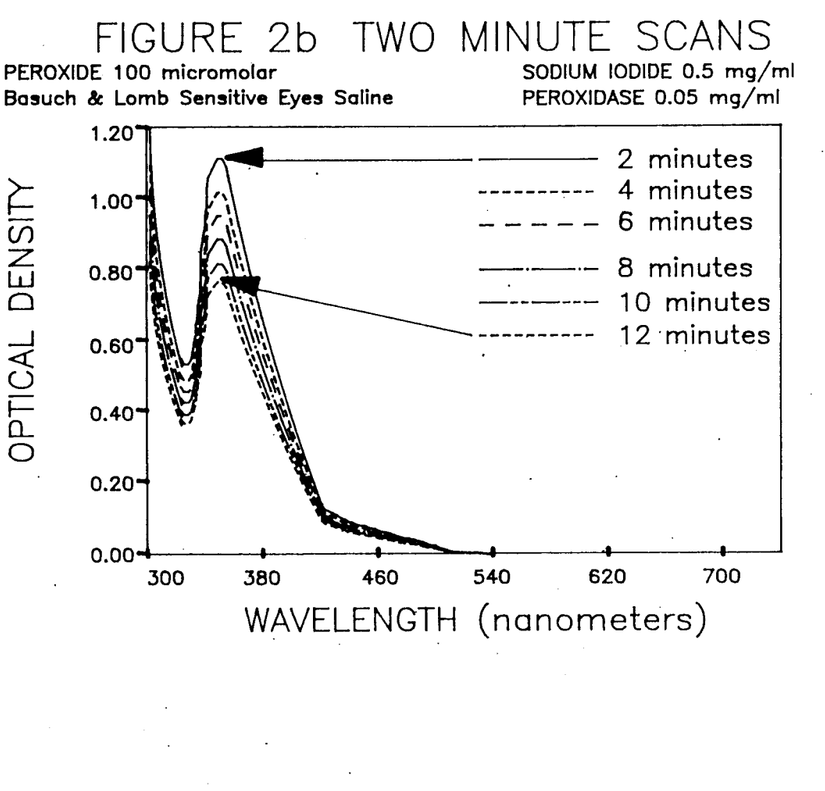
Figure 2C:
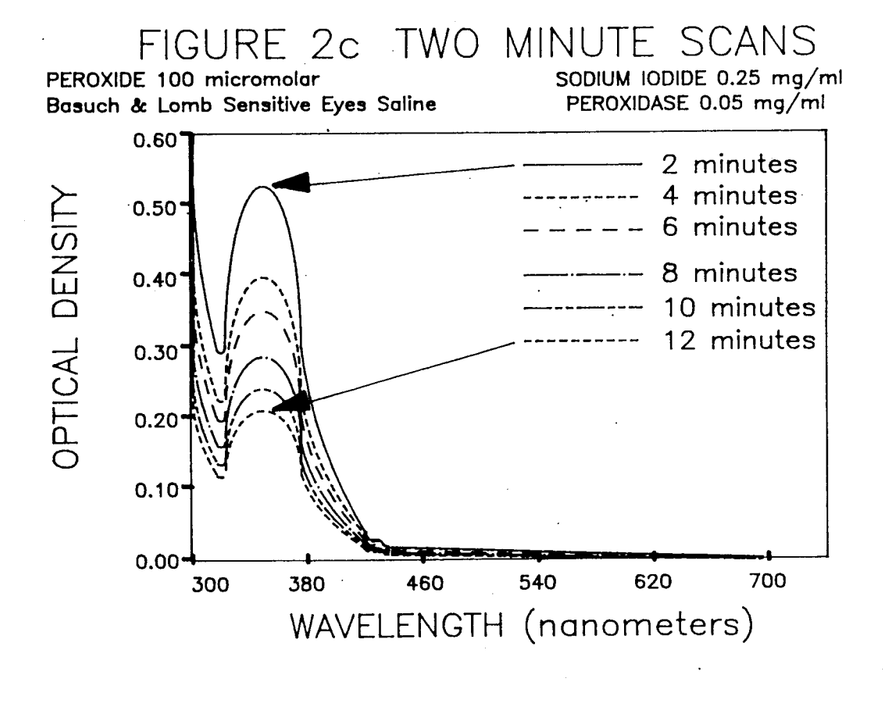
Figure 2D:
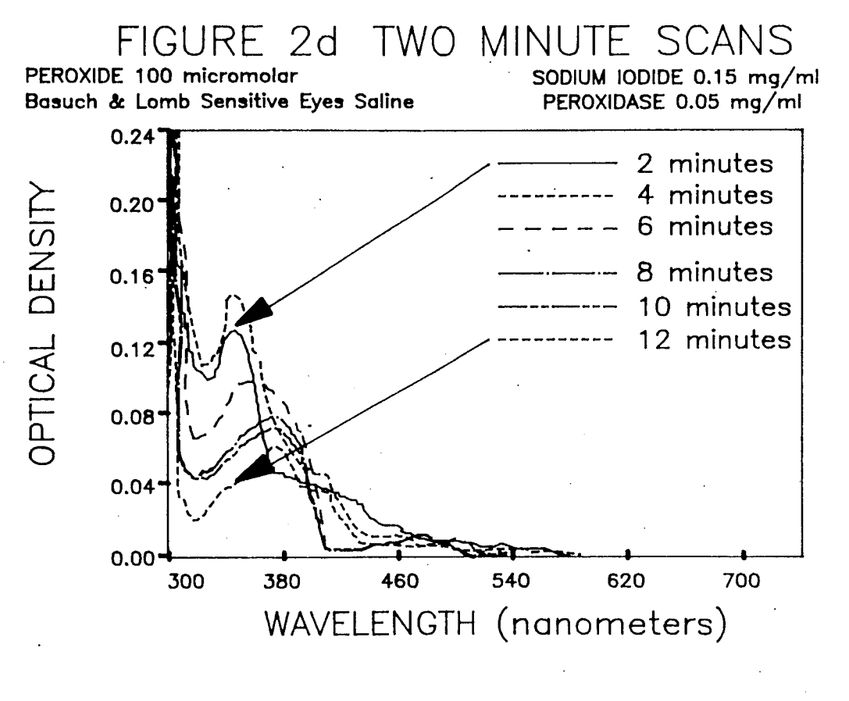
Figure 2E:
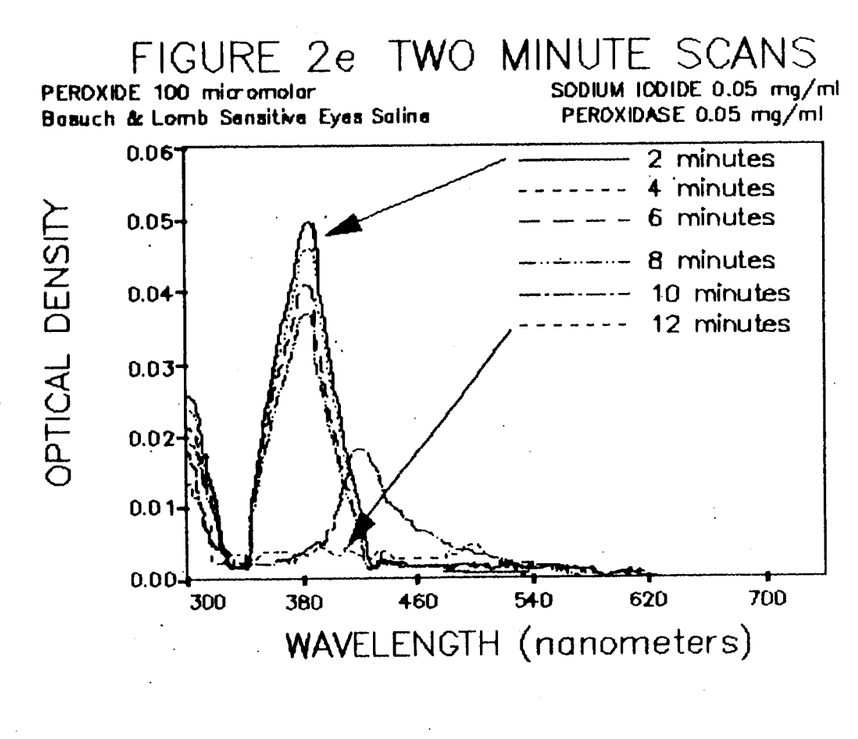

FIGS. 2 and 2e demonstrate one way in which the color can be caused to increase and then decrease to a noncolored condition. The conditions used for this measurement were as shown below:

| Component | Concentration |
|---|---|
| peroxidase | 0.05 mg/ml |
| peroxide | 100 micromolar |
| sodium phosphate-pH 7.0 | 10 millimolar |

Concentration of Reagents For FIGS. 2a-2e

| | FIG. Number | | | | | |
|---|---|---|---|---|---|---|
| | 2 | 2a | 2b | 2c | 2d | 2e |
| mg/ml of iodide | 1.5 | 1.0 | 0.5 | .25 | .15 | 0.15 |

As the concentration of iodide is decreased three things occur: (1) the intensity of the maximum absorbance decreases from 2.085 O.D. in FIG. 2 to 0.043 in FIG. 2e, (2) the absorbance maximum shifts from 355 nm in FIG. 2 to 395 nm in FIG. 2e, and (3) the % decrease over a ten minute period of the maximum absorbance in FIG. 2 is 16% as compared to 80% in FIG. 2e. This allows the formulation of components so that the resulting solution appears colored to the user during the disinfection cycle and then turns colorless after the period of disinfection. FIG. 2f shows the maximum color formed at each of the iodide concentrations above. It is clear that the amount of color formed can be controlled by adding defined amounts of iodide for a given peroxide concentration and a given environment.

EXAMPLE 3

Simple organic acids and salts were included in the reaction mixture to determine their effect on both the temporal and quantitative aspects of color formation. The reference reaction against which all reaction were compared contained the following components.

| | |
|---|---|
| peroxidase | 0.05 mg/ml |
| peroxide | 100 micromolar |
| sodium iodide | 0.15 mg/ml |
| sodium phosphate-pH 7.0 | 10 millimolar |

The UV-VIS spectrum was scanned from 200 to 450 nm six times during a ten minute period. Other components were added to the reference reaction to determine their effect upon the amount and time course of color increase which was centered at 350 nm. Lactic acid, malonic acid, citric acid, quiacol to concentrations of 0.1% by weight, did not act to reduce the intensity of color increase nor to increase the rate of disappearance of color. Concentrations of sodium chloride up to 0.20 molar acted to reduce the intensity of color but not the time course of color formation. In fact, 10 millimolar borate, pH 7.0 in combination with 0.15 molar sodium chloride and 0.01% sorbic acid eliminated color from the reference reaction.

What I claim is:

1. A method for controlling the formation of color in a peroxide disinfecting system including, in combination, a peroxidase, peroxide and an iodide salt formulated in a desired ratio to cause disinfection within an aqueous medium comprising the steps of adding to said combination a decolorizer selected from the group consisting of: sorbic acid, malonic acid, boronic acid, sodium chloride and peroxide where said peroxide is in an amount above the peroxide level needed for said disinfection.

2. A method as defined in claim 1 wherein the formulated concentration of peroxide lies in a range between 0.00003 and 0.0003% and wherein said decolorizer consists of a supplemental concentration of peroxide in a range between 0.001 and 0.3%.

3. A method for controlling the formation of color in a peroxide disinfecting system including, in combination, a peroxidase, peroxide and an iodide salt formulated in a desired ratio to cause disinfection within an aqueous medium comprising the steps of introducing a neutralizing agent into said aqueous medium for interrupting the reaction between the aforesaid components of the disinfecting system upon reaching a minimum acceptable color threshold level.

4. A method as defined in claim 3 wherein said neutralizing agent is selected from the class consisting of pyruvic acid, copper ions, platinum and catalase.

5. A method for controlling the formation of color in a peroxide disinfecting system including, in combination, a peroxidase, peroxide and an iodide salt formulated in a desired ratio to cause disinfection within an aqueous medium comprising the step of limiting the level of said iodide salt to a concentration corresponding to a minimum acceptable color threshold level and adding at least a second donor molecule other than an iodide salt as a supplement to cause additional disinfection.

6. A method as defined in claim 5 wherein said second donor molecule is selected from the class consisting of tyrosine and phenol.

7. A color controlled disinfection peroxide cold sterilization composition comprising a peroxidase, peroxide, and iodide salt and a decolorizer selected from the class consisting of sorbic acid, malonic acid, boronic acid and sodium chloride.

8. A color controlled disinfection peroxide cold sterilization composition comprising a disinfectant consisting essentially of a peroxidase, peroxide, an iodide salt and a decolorizing agent adapted to neutralize said disinfectant in an aqueous medium over a controlled time period.

9. A composition as defined in claim 8 wherein said decolorizing agent is selected from the class consisting of pyruvic acid, copper ions, platinum and catalase.

10. A method for controlling the formation of color in a peroxide disinfecting system including, in combination, a peroxidase, peroxide and an iodide salt formulated in a desired ratio to cause disinfection within an aqueous medium comprising the step of limiting the level of said iodide salt to a concentration corresponding to a acceptable minimum color threshold level.

11. A method as defined in claim 1, 3, 5, or 10 for hygenically treating the human oral cavity and dentures.

* * * * *